United States Patent [19]

Umemura

[11] Patent Number: 5,283,090

[45] Date of Patent: Feb. 1, 1994

[54] PORTABLE URINE OR OSTOMY BAG

[75] Inventor: Yoshihiro Umemura, Kyoto, Japan

[73] Assignee: Unitika Ltd., Hyogo, Japan

[21] Appl. No.: 708,567

[22] Filed: May 31, 1991

[30] Foreign Application Priority Data

Jun. 1, 1990 [JP] Japan ............... 2-144934

[51] Int. Cl.$^5$ ............ B61F 5/44; B32B 27/00; B32B 13/12
[52] U.S. Cl. ............... 428/35.4; 428/421; 428/422; 428/452; 428/451; 428/913; 604/332
[58] Field of Search ......... 428/421, 422, 451, 452, 428/913, 36.1, 35.4; 604/332, 333

[56] References Cited

U.S. PATENT DOCUMENTS

| | | | |
|---|---|---|---|
| 4,762,738 | 9/1988 | Keyes et al. | 428/34.3 |
| 4,826,493 | 5/1989 | Martini et al. | 428/516 |
| 4,950,545 | 8/1990 | Walter et al. | 428/452 |

FOREIGN PATENT DOCUMENTS

| | | |
|---|---|---|
| 0079248 | 5/1983 | European Pat. Off. . |
| 54-139679 | 10/1979 | Japan . |
| 1-221240 | 9/1989 | Japan . |

*Primary Examiner*—P. C. Sluby
*Attorney, Agent, or Firm*—Sughrue, Mion, Zinn, Macpeak & Seas

[57] ABSTRACT

ABSTRACT OF THE DISCLOSURE

A multi-layered sheet is disclosed, comprising a film substrate or sheet substrate which swells, disperses or dissolves in water, which has a fluorine-type or silicone-type water repellent coated on one side of the substrate.

4 Claims, No Drawings

PORTABLE URINE OR OSTOMY BAG

FIELD OF THE INVENTION

The present invention relates to a multilayered sheet, one side of which is water-impermeable but which as a whole becomes water-dispersible or water-swellable when water comes into contact with the other side of the sheet and penetrates thereinto.

BACKGROUND OF THE INVENTION

A known material which is both impermeable to water and which is soluble or dispersible in water is one which comprises a combination of polyvinyl alcohol and a gelation accelerator for polyvinyl alcohol. Specifically, such a material is composed of a polyvinyl alcohol film having formed thereon an absorption and retention layer constituted by a powder of a highly water-absorptive polymer and a powder of a gelation accelerator for polyvinyl alcohol. A sanitary napkin utilizing this material has been proposed (JP-B-59-13213, corresponding to U.S. Pat. No. 4,333,464). (The term "JP-B" as used herein means an "examined Japanese patent publication".) This sanitary napkin is considered to function as follows. The gelation accelerator for polyvinyl alcohol dissolves in the water contained in menstrual blood absorbed by the absorption and retention layer, and the resulting aqueous solution of the gelation accelerator wets the polyvinyl alcohol film to form a temporary insoluble gel. Thus, the sanitary napkin can exhibit a leakage preventing effect. When this napkin is immersed in a large quantity of water of water, the concentration of the gelation accelerator is lowered and, as a result, the gel collapses and becomes water-soluble or water-dispersible.

In the above-described sanitary napkin, the concentration in menstrual blood of the gelation accelerator for polyvinyl alcohol is an important point in order for the polyvinyl alcohol film to undergo gelation with the aid of the gelation accelerator. Although the range of gelation accelerator concentrations that can cause gelation varies depending on the kind of the gelation accelerator, it has been difficult with such a system to always and completely prevent the leakage of menstrual blood.

In JP-A-63-181758 (the term "JP-A" as used herein means an "unexamined published Japanese patent application") (corresponding to U.S. Pat. Nos. 4,762,738, 4,830,187 & 4,930,942), an ostomy pouch is proposed which can be thrown away by means of flushing in an ordinary toilet. This ostomy pouch is produced by joining a front panel consisting of a water-swellable and cold water-insoluble film material having a water-resistant layer laminated thereto to a rear panel consisting of a water-swellable and cold water-insoluble film material having a layer laminated thereto. Since this ostomy pouch employs water-swellable and cold water-insoluble film materials on the inner side thereof, it becomes viscous upon contact with water in a toilet stool to thereby pass through the drainage piping system.

However, such an ostomy pouch employing a water-swellable and cold water-insoluble film material has the problem that since its inner-side film layer is water-swellable, complete water resistance cannot be obtained when feces, etc., having a high water content are to be held therein, although it is possible to hold substances with a low water content.

SUMMARY OF THE INVENTION

The present inventor conducted intensive studies in order to eliminate the above-described drawbacks of the prior art products. As a result, it was found that by providing a layer of a fluorine-containing or silicone-type water repellent coating on one side of a water-soluble film or sheet, the coating layer side of the sheet becomes water-resistant and when water comes into contact with the other side of the sheet, the water penetrates into the sheet and the whole sheet is dispersed in water. The present invention has been completed based on this finding.

Accordingly, an object of the present invention is to provide a multi-layered sheet, one side of which is water-impermeable aqueous solutions and the whole of which, when the other side of the sheet is brought into contact with water, becomes water-dispersible or water-swellable in the presence of water, thereby eliminating the drawbacks of the conventional techniques.

Other objects and effects of the present invention will be apparent from the following description.

The present invention provides a multi-layered sheet comprising a film or sheet substrate which swells in water or is dispersible or soluble in water having formed on one side of the substrate a coating of a fluorine-containing or silicone-type water repellent.

The characteristic feature of the multi-layered sheet of the present invention resides in that one side of the sheet is water-impermeable and does not allow water or aqueous solutions to leak out but when water comes into contact with the other side of the sheet the whole sheet becomes water-dispersible or water-swellable Therefore, the multi-layered sheet of this invention can be used not only in the sanitary material but has applications in many fields, so that it will have a considerable effect on many industries.

DETAILED DESCRIPTION OF THE INVENTION

In the present invention, the term "water-swellable" means a property that when a sheet or film is in contact with water, the material expands and gelates as a result of absorbing water, which sheet or film is impossible to maintain its figure under water stream such as stir. On the other hand, the term "water-dispersible" means a property of a sheet or film to disperse in water in the state of being broken into pieces of milimeters or smaller under stream, which material does not absorb water to be distinguishable from water-swellable one. Further, the term "water-soluble" means a property of a sheet or film to completely dissolve in water into liquid state.

The film or sheet material for use as a substrate in this invention is not particularly limited as long as it swells in water or is dispersible or soluble in water. However, a material which is not rendered water-insoluble upon drying or heat treatment after coating should be selected for use as the substrate. Also, the film or sheet material for use as a substrate is not limited in terms of the polymerization degree thereof, as long as a flexible film or sheet is formed thereby. Examples of the film or sheet material for use in this invention include polyvinylpyrrolidone, polyacrylamide, polyvinyl ethers, polyethylene oxide, methyl cellulose, ethyl cellulose, carboxymethyl cellulose, hydroxyethyl cellulose, polyvinyl alcohol, polyacrylic acid and polymethacrylic acid and sodium, potassium, magnesium or calcium salts thereof, isobutene-maleic anhydride copolymers and salts thereof, and the like.

The substrate appropriate for use in the invention preferably has a thickness of 10 to 200 $\mu$m, more preferably 20 to 100 $\mu$m.

Applications of fluorine-containing water repellents began with their use for the surface treatment of fibers. Since then, water repellents of this type have been used to treat surfaces of various materials. The fluorine-containing water repellent employed in the present invention may be any conventionally utilized one. Examples thereof include products of the emulsion polymerization of tetrafluoroethylene such as polytetrafluoroethylene (PTFE), products of the polymerization of a monomer obtained by incorporating a perfluoroalkyl group of $C_1$ to $C_{20}$, preferably $C_2$ to $C_{10}$, into the ester group of a methacrylate or obtained by the copolymerization of such a monomer with other monomer(s) obtained by incorporating an alkyl group of $C_1$ to $C_{20}$ without fluorine atom into the ester group of a methacrylate, products of the polymerization of a perfluorovinyl ether, and the like.

Silicones are materials having excellent weatherability, durability, and unusual surface activity such as water repellency, and they have been utilized, like fluorine-containing water repellents, as fiber-treating agents in various fields. Examples of the silicone-type water repellent for use in this invention include those containing a silicone resin as a major component and reactive silicone compounds which contain methylhydroxypolysiloxane as a major component and undergo network formation with the aid of a catalyst, whereby orientation of hydrophobic methyl groups in the resin molecule occurs to increase, repellency of the water repellent as a result of crystallization. Examples of the catalyst used for network formation of the reactive silicone compounds include organic acid salts of metals such as lead, tin, zinc, cobalt, manganese, chromium, zirconium and titanium.

The coating layer of the water repellent preferably has a thickness of 0.2 to 10 $\mu$m, more preferably 0.5 to 5 $\mu$m.

In the case where the water repellent used for producing the multi-layered sheet of this invention is of the aqueous emulsion type, application of this water repellent to a film or sheet may result in breakage of the film or sheet at the time of coating. For this reason, use of a solvent-based water repellent is preferred, which contains a fluorine series resin or a silicone series resin in an amount of 0.1 to 80%, preferably to 50%, based on the total weight, being dissolved in an organic solvent such as 1,1,1,-trichloroethane, trichlorotrifluoroethane, ethyl acetate, n-butyl acetate, acetone, methylethyl ketone, methylisobutyl ketone, dioxane, tetrahydrofuran, toluene, xylene, n-hexane, ethanol, butanol, etc.

The multi-layered sheet of the present invention can be easily produced by coating the above-described water repellent using any conventional known technique on one side of a film or sheet which swells in water or is dispersible or soluble in water, drying it in air at a room temperature to 100° C. and heating the same in air at 100 to 150° C. for 1 to 30 min. Thus heat treatment results in orientation of water repellent resin molecule to increase repellent effect.

If the strength of this multi-layered sheet alone is insufficient for a particular application, a nonwoven, woven, or knit fabric made from a material having good dispersibility in water, such as carboxymethyl cellulose, may be used as a reinforcing material for the sheet on the side opposite to the side coated with the water repellent material.

The multi-layered sheet of this invention can be used for producing a sanitary material such as a disposable diaper, a sanitary napkin, or the like, in which case the multi-layered sheet is used with the water repellent-coated side being in contact with the body. Moreover, it can also be used for manufacturing a portable urine bag or an ostomy bag, with the water repellent-coated side of the sheet being inside. A sanitary napkin employing the multi-layered sheet of this invention and an absorption layer superposed on the water repellent-coated side of the sheet has been ascertained to have significantly improved usability as compared with conventional ones and to show excellent effects, because the multi-layered sheet functions as a leakage-preventive material and it can then be dispersed or swelled in water when the sanitary napkin is discarded.

Although the coating side of the multi-layered sheet of this invention is insoluble in water at ordinary temperature or at a temperature around body temperature, the substrate material is dissolved, dispersed or swelled in water below about 40° C. when water penetrates into the sheet from the side which has no coating.

The present invention is explained below in more detail with reference to the following examples, which should not be construed as limiting the scope of the invention.

EXAMPLE 1

In 100 ml of water there was dissolved 15 g of a polyvinyl alcohol (polymerization degree: 1,800, saponification degree: 87 to 88%) (UP-180, manufactured by Unitika Ltd., Japan). This solution was cast on a glass plate and dried in air at 40° C. for one night. Over the whole surface of one side of the thus-obtained film (thickness: about 100 $\mu$m) which had an area of 100 cm$^2$, 0.6 ml of a fluorine-containing water repellent (trade name Asahi Guard AG-650, manufactured by Asahi Glass Co., Ltd., Japan) was coated by using coating-rod to yield a thin layer with a thickness of about 2 $\mu$m. The resulting sheet was dried in air at 30–40C. for about one hour and then heat-treated at about 100–110° C. for 10 minutes. The thus-obtained multi-layered sheet was fabricated into a bag by heat sheel method in such a manner that the coating side of the sheet faced inside.

COMPARATIVE EXAMPLE 1

The same procedures as in Example 1 were repeated except that the polyvinyl alcohol film was heat-treated at about 100–110° C. for about 10 minutes without coating a layer of the water repellent.

EXAMPLE 2

The same procedures as in Example 1 were repeated except that the polyvinyl alcohol (UP-180) was replaced with another polyvinyl alcohol (polymerization degree: 1,700, saponification degree: 95.5 to 97.5%) (UF-170M, manufactured by Unitika Ltd.).

COMPARATIVE EXAMPLE 2

The same procedures as in Example 2 were repeated except that the polyvinyl alcohol film was heat-treated at about 100–110° C. for about 10 minutes without coating a layer of the water repellent.

EXAMPLE 3

The same procedures as in Example 1 were repeated except that the polyvinyl alcohol (UP-180) was replaced with another polyvinyl alcohol (polymerization degree: 1,800, saponification degree: 87 to 89%) (E-180, manufactured by Unitika Ltd.).

COMPARATIVE EXAMPLE 3

The same procedures as in Example 3 were repeated except that the polyvinyl alcohol film was heat-treated at about 100–11020 C. for about 10 minutes without coating a layer of the water repellent.

EXAMPLE 4

The same procedures as in Example 1 were repeated except that the water repellent (AG-650) was replaced with another fluorine-containing water repellent (Asahi Guard AG-610, manufactured by Asahi Glass Co., Ltd.).

EXAMPLE 5

The same procedures as in Example 1 were repeated except that the water repellent (AG-650) was replaced with another silicone-type and solvent-based water repellent (POLON-T, manufactured by Shin-Etsu Chemical Co., Ltd., Japan).

REFERENCE EXAMPLE

Into each of the bags obtained in Examples 1 to 5 and Comparative Examples 1 to 3 was placed 30 ml of distilled water. The resulting bags were examined for any changes. The results obtained are summarized in Table 1.

Further, a 10 cm square portion of each of the sheets was added to 500 ml of distilled water. While the resulting water was being stirred, the squares were examined for any changes. The results obtained are summarized in Table 2.

TABLE 1

| | Water retention in bags |
|---|---|
| Example 1 | No leakage for 1 day or more |
| Example 2 | No leakage for 1 day or more |
| Example 3 | No leakage for 1 day or more |
| Example 4 | No leakage for 1 day or more |
| Example 5 | Leakage in 1 hr. |
| Comp. Example 1 | Leakage in 2 min. |
| Comp. Example 2 | Leakage in 2 min. |
| Comp. Example 3 | Leakage in 2 min. |

TABLE 2

| | Solubility |
|---|---|
| Example 1 | Dispersed in 20 min. |
| Example 2 | Dispersed in 30 min. |
| Example 3 | Dispersed in 60 min. |
| Example 4 | Dispersed in 20 min. |
| Example 5 | Dispersed in 20 min. |
| Comp. Example 1 | Dissolved in 5 min. |
| Comp. Example 2 | Dissolved in 5 min. |
| Comp. Example 3 | Dissolved in 5 min. |

As is apparent from Tables 1 to 2, all of the multi-layered sheets of this invention obtained in the above Examples showed sufficient water retention and solubility.

While the invention has been described in detail and with reference to specific embodiments thereof, it will be apparent to one skilled in the art that various changes and modifications can be made therein without departing from the spirit and scope thereof.

What is claimed is:

1. A portable urine bag or ostomy bag comprising a film substrate or sheet substrate which swells, disperses or dissolves in water on the outside and water repellent layer coated on the inside, said water repellent layer comprising a fluorine or silicone water repellent; wherein said fluorine water repellent is selected from polytetrafluoroethylene, a poly(meth)acrylate wherein all or part of the alkyl groups in the ester groups are substituted by a fluorine atom, and products of the polymerization of a perfluorovinyl ether; and said silicone water repellant is comprised of compounds containing a silicone resin as a major component or reactive silicone compounds which contain methylhydroxypolysiloxane as a major component and undergo cross-linking with the aid of a catalyst.

2. The portable urine bag or ostomy bas as in claim 1, wherein said substrate is a film or sheet selected from the group consisting of polyvinylpyrrolidone, polyacrylamide, polyvinyl ethers, polyethylene oxide, methyl cellulose, ethyl cellulose, carboxymethyl cellulose, hydroxyethyl cellulose, polyvinyl alcohol, polyacrylic acid and polymethacrylic acid and salts thereof, isobutene-maleic anhydride copolymers and salts thereof.

3. The portable urine bag or ostomy bas as in claim 2, wherein said substrate is a film or sheet of polyvinyl alcohol.

4. The portable urine bag or ostomy bag as in claim 1, wherein said water repellant is soluble in organic solvents.

* * * * *